(12) United States Patent
Dikovskiy et al.

(10) Patent No.: US 10,398,717 B2
(45) Date of Patent: Sep. 3, 2019

(54) PHARMACEUTICAL COMPOSITION BASED ON A HEPATOPROTECTOR AND PREBIOTIC, AND METHOD FOR ADMINISTRATING

(71) Applicants: Alexander Vladimirovich Dikovskiy, Moscow (RU); Boris Anatolievich Rudoi, Moscow (RU); Oleg Valentinovich Dorozhko, Moscow (RU)

(72) Inventors: Alexander Vladimirovich Dikovskiy, Moscow (RU); Boris Anatolievich Rudoi, Moscow (RU); Oleg Valentinovich Dorozhko, Moscow (RU)

( * ) Notice: Subject to any disclaimer, the term of this patent is extended or adjusted under 35 U.S.C. 154(b) by 0 days.

(21) Appl. No.: 15/363,303

(22) Filed: Nov. 29, 2016

(65) Prior Publication Data
US 2017/0071968 A1 Mar. 16, 2017

Related U.S. Application Data

(63) Continuation-in-part of application No. 15/240,249, filed on Aug. 18, 2016, now abandoned, which is a continuation of application No. 12/921,383, filed as application No. PCT/RU2008/000122 on Mar. 4, 2008, now Pat. No. 9,446,058.

(51) Int. Cl.
| | |
|---|---|
| A61K 31/70 | (2006.01) |
| A01N 43/04 | (2006.01) |
| A61K 31/7032 | (2006.01) |
| A61K 31/7016 | (2006.01) |
| A61K 31/702 | (2006.01) |
| A61K 31/575 | (2006.01) |
| A61K 31/685 | (2006.01) |
| A61K 31/683 | (2006.01) |
| A61K 31/357 | (2006.01) |
| A61K 9/00 | (2006.01) |
| A61K 36/28 | (2006.01) |
| A61K 45/06 | (2006.01) |
| A61K 31/52 | (2006.01) |
| A61K 31/66 | (2006.01) |
| A23L 33/10 | (2016.01) |
| A23L 33/21 | (2016.01) |
| A23D 7/005 | (2006.01) |
| A61P 1/16 | (2006.01) |

(52) U.S. Cl.
CPC .......... *A61K 31/7032* (2013.01); *A23D 7/005* (2013.01); *A23L 33/10* (2016.08); *A23L 33/21* (2016.08); *A61K 9/0053* (2013.01); *A61K 31/357* (2013.01); *A61K 31/52* (2013.01); *A61K 31/575* (2013.01); *A61K 31/66* (2013.01); *A61K 31/683* (2013.01); *A61K 31/685* (2013.01); *A61K 31/702* (2013.01); *A61K 31/7016* (2013.01); *A61K 36/28* (2013.01); *A61K 45/06* (2013.01); *A61P 1/16* (2018.01); *A23V 2002/00* (2013.01)

(58) Field of Classification Search
None
See application file for complete search history.

(56) References Cited

PUBLICATIONS

Fasano et al. Digestive Diseases and Sciences (1990), vol. 35, pp. 801-808.*
Donely Seminars in Avian and Exotic Pet Medicine (2004), vol. 13, pp. 8-15.*
Schumann Eur. J. Nutr. (2002), vol. 41, pp. 1/17-1/25.*
Calmus et al. Plepatology (1990), vol. 11, pp. 12-15,.*
Lindblad et al. Plepatology (1998), vol. 27, pp. 166-174.*
Sailer et al. Drugs (2001), vol. 61, pp. 2035-2063.*
Flora et al. AJG (1998), vol. 93, pp. 139-143.*
Stratton et al. Best Practice & Research Clinical Gastroenterology (2005), vol. 20, pp. 441-466.*

* cited by examiner

*Primary Examiner* — Patrick T Lewis
(74) *Attorney, Agent, or Firm* — Nadya Reingand; Yan Hankin

(57) ABSTRACT

The invention relates to medicine, hepatology and pharmacology and can be used for producing and using a pharmaceutical composition based on a hepatoprotector and a prebiotic for treating and preventing liver diseases which are caused by lipid-cholesterol exchange and selected from the following group: cholelitiasis mainly with cholesterol stones, alcoholic and non-alcoholic steatohepatitis, biliary cirrhosis, cholesterol imbibition gallbladder and drug-induced and toxic liver damage. The pharmaceutical composition is administered by mouth and contains a hepatoprotector and a prebiotic taken, as an active agent, in therapeutically effective doses. The invention contributes to the liver's functional recovery in a short time and prevents disease recidivation owing to the recovery of cholesterol exchange and intestinal biocenosis as a result of the synergistic interaction of a hepatoprotector and a prebiotic, thereby also preventing hepatoprotector side effects.

5 Claims, No Drawings

PHARMACEUTICAL COMPOSITION BASED ON A HEPATOPROTECTOR AND PREBIOTIC, AND METHOD FOR ADMINISTRATING

CROSS-REFERENCE TO RELATED APPLICATIONS

The present patent application is a continuation-in-part of U.S. patent application Ser. No. 15/240,249 "PHARMACEUTICAL COMPOSITION BASED ON A HEPATOPROTECTOR AND A PREBIOTIC, AND PRODUCTION AND APPLICATION THEREOF" filed Aug. 18, 2016, which is a continuation of the U.S. patent application Ser. No. 12/921,383 filed Sep. 7, 2010, which is National stage application of PCT application PCT/RU2008/000122 filed Mar. 4, 2008.

FIELD OF INVENTION

The invention relates to medicine, particularly to hepatology and pharmacology. It can be used for production and application of a pharmaceutical composition based on a hepatoprotector and a prebiotic for treatment and prevention of liver diseases selected from the following group: cholelithiasis, fatty hepatosis and nonalcoholic steatohepatitis, primary biliary cirrhosis, gallbladder cholesterosis, and drug-induced and toxic liver injury.

BACKGROUND OF THE INVENTION

The urgency of the issue is due to higher frequency and severity of diseases of liver, the main organ for detoxification of exogenous toxins. The increased incidence of liver diseases is caused by environmental troubles in most world regions.

An additional cause which is directly related to the effect of environmental factors is reduced immunity of the population, resulting in significant increase of infectious liver lesions, and first of all of viral hepatitises.

In the case of viral hepatitis, the source of infection is a sick person, and the infection transmission route is either fecal—oral or parenteral, depending on the type of virus—A, B, C, D, G, or E. Population's susceptibility to this infection is high.

Regardless of the sight of entry, the virus eventually gets in the liver where it has direct toxic effect on liver cells, combined with immune-mediated damage of cell membranes. In all forms of viral hepatitis, a serious frequent complication is disturbance of normal processes of formation and flow of bile, the so-called cholestatic syndrome accompanied by jaundice, it is most often manifested in the case of viral hepatitis A (VHA)—"enteric" viral hepatitis and enteric hepatitis E, wherein the frequency of jaundiced forms is 100%.

In severe forms of acute viral hepatitises (AVH) flow and exacerbations of chronic hepatisises, the disturbance of structure and functional activity of biliary ducts is one of the reasons of development of a severe complication—biliary cirrhosis.

In addition to viral hepatitises, a large share of liver diseases is due to the effect of food toxicants (alcohol, other toxic substances, and various medicinal agents).

One of the earliest pathological complications in toxic liver injury is steatohepatitis—the result of disturbance of the normal balance between the input of fats in the body and their metabolism.

It should be emphasized that disturbance of normal processes of formation and biliary passage of bile is one of widespread consequences of the effect of high doses of a number of drugs (antibiotics, sulfanilamides, chlorpromazine, histamine receptor and estrogen blockers, and cytostatics).

During the last decade, a so-called autoimmune hepatitis, the result of deep disturbance in the cell immunity system, is being diagnosed more and more often. Its most severe consequence is primary biliary cirrhosis.

Disturbance of bile production and excretion processes is most vividly pronounced in the form of cholelithiasis, wherein excessive accumulation (congestion) of bile in the gallbladder with subsequent formation of concrements (choleliths or gallstones) is observed.

In all of the above liver diseases, an important ethiologic and pathogenic factor is disturbance of normal processes of bile acids (BA) metabolism, one of the most important factors of normal digestion.

BAs are formed in liver from cholesterol (Hofmarm A. F. Bile acid secretion, bile flow and biliary lipid secretion in humans. Hepatologi, 1990; 12; 175; Meier P. J. The bile salt secretory polarity of hepatocytes, J. Hepatol. 1989; 9:124).

Main BAs detected in human bile are cholic acid (CA) (3a, 7a, 12a-trioxy-5b-cholanic acid), chenodeoxycholic acid (CDCA), deoxycholic acld (DCA) (3a, 12a-dioxy-5b-cholanic acid). Stereoisomeres of cholic and deoxycholic acids In the form of allocholic (ACA), ursodeoxycholic (UDCA) and lithocholic (LCA) acids have been detected in bile in considerably smaller quantities.

CA and CDCA, the so-called primary BAs, form in the liver during oxidation of cholesterol, and DCA and LCA form in the intestine from primary BAs due to the effect of enzymes of intestinal flora microorganisms.

Normal quantitative ratio of CA, CDCA and DCA in bile is 1:1:0.6.

In bladder bile BAs are mainly present in the form of binary compounds—conjugates. In the intestine, mainly in the ileum, BAs are absorbed into blood, return with blood to the liver and are again secreted within bile—this is the so-called portal-biliar circulation of BAs; therefore, 85-90% of the entire amount of Bas contained in bile are BAs absorbed in the intestine.

Portal-biliar circulation of BAs facilitates easy absorption of BA conjugates in the intestine, because they are water-soluble; in the process, 10-15% of the total amount of BA break down in the intestine due to the effect of enzymes of intestine flora microorganisms, and the products of their degradation are excreted with stool.

By emulsifying fats, BAs thus ensure absorption of insoluble fatty acids and cholesterol in the small intestine, as well as of vitamins B, K, E and calcium salts.

In addition, BAs have strong choleretic effect, stimulate intestinal motility, and also have bacteriostatic and anti-inflammatory effect. Taking the above into account, a possible component of the method for treatment and prevention of a number of pathologic conditions of the liver is the use of bile acid preparations, and first o all UDCA.

UDCA is a tertiary bile acid; it was first found in Chinese bear bile in 1902. UDCA has been used in medicine for several centuries. As long ago as in ancient China, dried bear bile was prescribed for treatment of stomach, intestine and liver diseases. UDCA is formed, due to the action of bacterial enzymes, from 7-keto-litocholic acid that enters the liver from the small intestine.

Herein, all chemical formulae of UDCA and hydrophobic CDCA are identical (C24H4O4).

Using UDCA for treatment of, among others, liver diseases results in a dose-dependent change of the above ratio of bile acids: UDCA becomes the main bile component whereas the content of CDCA and other BAs decreases. Lower accumulation of UDCA in bile is observed in patients with liver diseases, which may be related to reduced absorption due to reduced formation of endogenous micellae from bile acids in duodenal bile or to reduced secretion of bile acids themselves.

As has been stated earlier, UDCA and LCA are detected in human bile in very insignificant amounts (0.1%-5%).

Despite good absorption of UDCA in the intestine, its level in blood plasma remains relatively low due to fast liver clearance, because effective conjugation of UDCA with glycine, taurine, N-acetoglucosaine, glucuronic acid and sulfate takes place in the liver.

The effect of UDCA on cholesterol in bile is a complex one: it reduces cholesterol absorption in the intestine, its synthesis in the liver and secretion into bile. However, there is noticeable decrease of cholesterol level in blood due to the effect of UDCA.

UDCA and its conjugates that have not been absorbed in the small intestine are metabolized by indigenous bacteria in the small intestine distal area and in the colon.

In the intestine, UDCA is broken down and dehydroxylated into lithocholic acid (LCA). LCA, whose content in human blood is very low, is formed in the small intestine due to the action of microflora during the process of utilization of numerous fats; from the small intestine LCA enters the colon and rectum, where it is partially absorbed, and enters the liver.

In the liver LCA bonds with sulfate anions and then with glycine and taurine, and this way is released in bile. Its derivatives are little absorbed in the intestine and excreted with stool, Such process is an efficient mechanism for elimination of toxic LCA from the body, CDCA determines decrease of activity of A-oxyreductase 3-hydroxy-3-methylglutarylcoenzyme—an enzyme that participates in the synthesis of cholesterol; it also facilitates decrease of cholesterol absorption in the intestine, which results in changing the ratio of bile acids and cholesterol towards prevailing of CDCA bile acids in the common pool.

The above mechanism predetermines the use of CDCA when dissolving gallstones that mainly consist of cholesterol.

Deoxycholic acid (DCA) is a bile acid that is formed in person's intestine due to action of intestine microflora enzymes, absorbed into blood and secreted by the liver with bile. It is assumed that hydrophobic DCA salt can be the link between disturbed intestinal motility and bile lithogenicity. The main bile acids in humans are CA and CDCA—primary bile acids synthesized in the liver from cholesterol.

Secondary DCA is formed from cholic acid in the small intestine distal areas and in the colon due to action of intestine microflora enzymes, namely, bacterial 7-alpha-dehydroxylase. DCA is partially absorbed from the intestine and involved in recirculation of bile acids after its conjugation with taurine or glycine in the liver.

Increase of the transit time in the intestine increases DCA formation as a result of bacterial metabolism, while decrease of the transit time has the opposite effect.

As a result, the amount of DCA varies within a wide range—from 10% to 30% of the total pool of bile acids. Recently it has been proved that patients with cholelithiasis have increased number of gram-positive anaerobic bacteria, and their 7-alpha-dehydroxylase activity in the colon is higher compared to healthy patients.

In the process, a correlation of slower transit through the intestine, higher DCA share, bile oversaturation with cholesterol and concrement formation has been found. It is assumed that DCA facilitates bile lithogenicity and concrement formation by slowing the transit time through the intestine, which in turn increases cholesterol absorption and, via the positive feedback mechanism, facilitates the formation of DCA itself. In addition, DCA can increase cholesterol secretion into bile by acting on the canalocular membrane of hepatocyte, where cholesterol is located in sphyngomyelin domains, and also increase cholesterol crystallization in bile, destabilizing vesicles with cholesterol.

In bladder, bile BAs are mainly present in the form of binary compounds—conjugates, As the result of BA conjugation with amino acid, glycine, glycocholic (GCA) or glycochenodesoxycholic (GCDCA) acid is formed. In BA conjugation with taurine (2-aminoethan-sulfoacid $C_2H_7O_3N_5$), the product of cycteine amino acid degradation, taurocholic (TCA) or taurodesoxycholic (TDCA) add is formed.

BA conjugation includes stages of formation of CoA-BA esters, and linkage of the BA molecule with glycine or taurine by means of amide bond, with the participation of lysosomal enzyme of acyltransferaze. The ratio of glycine and taurine conjugates of BA in bile, 3:1 on average, can vary depending on the composition of food and on the hormonal status of the organism.

Thus, disturbance of bile acids metabolism is an important pathogenic factor of development of a number of liver diseases.

Known is the method for treatment of the above liver diseases that consists of using UDCA preparations in the form of mono- or complex therapy (RU 2002123352 A of 03.27.2004).

Also known is the method for treatment of liver diseases by using CDCA preparations in complex therapy, see Register of Medicinal Agents of Russia. Encyclopedia of Drugs]. G. L. Vyshkovskiy Editor-in-Chief. M., "RLS"-2006, 2005, pp. 895-896),

SUMMARY OF THE INVENTION

The present invention comprises a pharmaceutical composition for a treatment and prevention of recurrences of liver diseases in human caused by a disturbance of lipid-cholesterol metabolism, wherein the liver diseases are selected from a group including cholelithiasis with mainly cholesterol stones, alcoholic and nonalcoholic steatohepatitis, primary biliary cirrhosis, gall bladder cholesterosis, and drug-induced and toxic liver injury, the composition comprising a mixture of a hepatoprotector and a prebiotic combined together in effective doses in a ratio of 1:2 to 1:250 by mass of pure substances, the mixture being taken by a person orally, the doses leading to a restoration of liver functions and prevention of exacerbations of liver diseases, wherein the hepaprotector comprises ursodeoxycholic acid (UDCA) and the prebiotic comprises lactitol.

In some aspects, the hepatoprotector further comprises amino acids.

In some aspects, the hepatoprotector further comprises active components of milk thistle plant extracts.

In some aspects, the hepatoprotector further comprises essential phospholipids.

In some aspects, the hepatoprotector further comprises other bile acids or bile acid salts.

In some aspects, the bile acids or bile acid salts are selected from the group consisting of chenodesoxycholic acid (CDCA), desoxycholic add (DCA), lithochioic acid (LCA), taurodesoxycholic acid (TDCA), hyodeoxycholic add (HDCA), taurocholic acid (TCA), glycochloic acid (GCA), and combinations thereof.

In some aspects, the prebiotic further comprises fructooligosaccharides.

In some aspects, the prebiotic further comprises maltooligosaccharides.

In some aspects, the prebiotic further comprises galactooligosaccharides.

In some aspects, the prebiotic further comprises xylooligosaccharides,

In some aspects, the prebiotic is lactulose in a ratio of 1:2 by mass of pure substances.

In some aspects, the hepatoprotector further comprises essential phospholipicis selected from a group consisting of phosphatidylcholin, phosphatidylethanolamine and phosphatidylinositol, in a ratio of the essential phospholipids and the prebiotic is from 1:0.1 to 1:100 by mass of pure substances.

In some aspects, the hepatoprotector further comprises active components of milk thistle plant extracts selected from silimarin or silibin, and a ratio of the active components of milk thistle plant extracts and the prebiotic is from 1:0.1 to 1:100 by mass of pure substances.

In some aspects, the composition is made in the form of tablets, granules, globules, powders or capsules, suspensions, pastes, syrups, mulsion, or gels intended for oral administration 2-3 times a day.

In some aspects, the hepatoprotector and he prebiotic are taken in effective doses in a ratio of 1:2 to 1:50 by mass of pure substances.

Also disclosed is a method for treating and preventing recurrences of liver diseases in humans caused by a disturbance of lipid-cholesterol metabolism, wherein the liver diseases are selected from a group including cholelithiasis with mainly cholesterol stones, alcoholic and nonalcoholic steatohepatitis, primary biliar cirrhosis, gall bladder cholesterosis, and drug-induced and toxic liver injury, the method comprising administering a composition orally on a patient, wherein the composition comprises a mixture of a hepatoprotector and a prebiotic combined together in effective doses in a ratio of 1:2 to 1:250 by mass of pure substances, wherein the hepaprotector comprises ursodeoxycholic acid (UDCA) and the prebiotic comprises lactitol, and delivering the UDCA and lactitol to the patient's liver.

In some aspects, a therapeutic effect on the patient's liver develops within 1 month.

In some aspects, a therapeutic effect on the patient's liver develops within 3 months.

In some aspects, the administering occurs 3 times daily.

In some aspects, the UDCA:lactitol ratio is between 1:2 and 1:250.

DETAILED DESCRIPTION OF THE PREFERRED EMBODIMENT

According to prior art treatment methods, the therapeutic effect only develops after a prolonged period (from several months to 6-12 months) of using medications, and often requires essentially taking them for life.

To a large extent this is due to the fact that the use of BA preparations as monotherapy cannot eliminate completely such important pathogenic factor as intestinal dysbiosis and complex systemic disturbances of metabolism it causes.

As drugs with hepatoprotective properties, one has long been using substances with different structure and mechanisms of action; a lot of professionals challenge the appropriateness of considering them true hepatoprotectors.

In particular, the class of so-called essential phospholipids is often added to them.

Phospholipids, or phosphoglycerides, are highly specialized lipids; they are important fundamental components of cell membranes and membranes of structural elements of cells, such as mitochondria, and can be called "essential" (irreplaceable) for growth, development and proper functioning of all somatic cells. In addition to their role in building cell membranes, one can say that phospholipids are important components of lipoproteins, "lung surfactants" and bile. They take part in operation of the nervous system and in membrane enzyme reactions, and play an important role in metabolism and oxidation processes. As part of lipoproteins, phospholipids affect the level of cholesterol concentration in blood.

Phospholipids located in trombocites participate in the blood clotting process, which in the end demonstrates their effect on the protective function of blood and on hemodynamics in the organism of mammals and humans. Phospholipids chemical structure, difility and presence of charged groups determine the uniqueness of their physiological properties.

The main function of phospholipids is forming a double lipid layer in cell membranes. The structure and function of cell membranes are extremely important for person's health. The feeling of general malady, disturbance of functions and various diseases can in many cases be explained by damage to or instability of membranes. By introducing phospholipids one can affect membrane functions related to membrane proteins and correct them, at least to a certain extent, and sometimes completely correct the disturbed function.

Essential phospholipids mainly penetrate liver cells, embed into hepatocite membranes, normalize liver functions and metabolism of lipids and proteins, facilitate activation and protection of phospholipid-dependent enzyme systems, improve the detoxification function of the liver, restore its cell structure, improve regeneration, and inhibit formation of connective tissue in it.

The preparation reduces the level of energy consumption in the liver, converts neutral fats and cholesterol to easily metabolized forms, and stabilizes bile physical and chemical properties.

Essential phospholipids normalize intestinal digestion not only of fats but also, indirectly, of solid food due to restoration of the structure of liver cells, which results in normalization of bile formation and excretion (Gurevich, K. G., Essential Phospholipids in Treatment of Liver Diseases, see High Quality Medical Practice, 2002, No. 4, pp, 108-111).

Another representative of the group of substances with hepatoprotective properties is milk thistle plant extract as the main active substance in silimarin. It has hepatoprotective, regenerative and detoxification effect.

It neutralizes free radicals in the liver and prevents the destruction of cell structures. It specifically stimulates RNC polymerase and activates the synthesis of structural and functional proteins and phospholipids in damaged hepatocites. It stabilizes cell membranes, prevents exit of intracellular components (transaminases) and accelerates regeneration of liver cells. It inhibits penetration of some hepatotoxic substances (death cup mushroom poison) into the cell.

Clinical pharmacology: improves the general well-being of patients with liver diseases, reduces subjective complaints—weakness, feeling of weight in the right hypochondrium, loss of appetite, vomiting and skin itch, and normalizes laboratory parameters—the activity of transaminases, gamma glutamyl and alkaline phosphotase, and bilirubin level. In prolonged use it increases the life expectancy of patients with liver cirrhosis.

A number of amino acids or their derivatives are also often considered preparations of the hepatoprotective series.

The best known of them is ademethionine, see Register of Medicinal Agents of Russia, Encyclopedia of Drugs, G. L, Vyshkovskiy Editor-in-Chief, M., "RLS"-2006, 2005, p, 51.

This preparation makes up for the deficiency of ademethionine and stimulates its production in the body, first of all in the liver and brain. The S-adenosil-L-metionine (ademethionine) molecule donates the methyl group in reactions of methylation of phospholipids of cell membranes of proteins, hormones, neuromediators, etc. (transmethylation). It is the precursor of physiological thyol compounds—cyctaine, taurine, glutathione (provides a redox mechanism of cell detoxification), coenzyme A, etc, in transsulfatation reactions. After decarboxylation, it participates in processes of aminopropylation as the precursor of polyamines—putrescine (stimulator of cell regeneration and proliferation of hepatocites), spermidine and spermine that are part of ribosomes structure.

It has anticholestatic effect and is effective in the intralobial version of cholestasis (disturbance of bile synthesis and flow). The anticholestatic effect is due to increased motility and polarization of hepatocite membranes because of stimulation of the synthesis of phosphatidylcholine in them. This improves the function of hepatocites of transport systems of bile acids (BAs) associated with membranes and facilitates BA passage into the bile excretion system. It stimulates BA detoxification—increases the content of conjugated and sulfated BAs in hepatocites. Conjugation with taurine increases BAs solubility and elimination from hepatocyte. Sulphatation makes possible elimination by kidneys and facilitates hepatocite passage through the membrane and excretion with bile. In addition, sulphated BAs protect liver cell membranes from toxic action of non-sulphated BAs (present in high concentrations in hepatocites intrahepatic cholestasis).

In patients with diffuse liver diseases (cirrhosis, hepatitis) with intrhepatic cholestasis syndrome it reduces the intensity of skin itch and changes of biochemical indices, including the level of conjugated bilirubin, ALP activity, aminotransferases, etc.

The therapy was accompanied by disappearance of asthenic syndrome in 54% of patients and the decrease of its intensity in 46% of patients. The aritiasthenic, anticholestatic and hepatoprotective effects continued for 3 months after the treatment was stopped. Their efficiency in the case of hepatopathies caused by hepatotoxic medicinal agents (paracetomol, etc.) has been demonstrated. As a result of treatment of patients with opiate drug addiction accompanied by liver injury, regression of clinical manifestations of abstinence, improved functional condition of the liver and microsomal oxidation processes, and the anti-depressant effect were observed.

The use: intrahepatic cholestasis; liver injuries—toxic, including alcoholic, virus and drug-induced (antibiotics; anticancer, antituberculous and antivirus preparations; tricyclic antidepressants; and oral contraceptives); cirrhotic and pre-cirrhotic conditions; encephalopathy, including encephalopathy associated with hepatic failure (alcoholic, etc.); depressive and abstinence syndromes.

In addition to directly affecting the liver tissue, ademethionine has a number of additional pharmacological effects, such as antidepressant action (develops during the first week and stabilizes during the second week of treatment). This preparation is also used empirically osteoarthrytises; this is accompanied by reduced pain syndrome, by stimulation of the synthesis of proteoglycans, and by partial regeneration of cartilaginous issue.

However, the use of essential phospholipids in therapy of liver diseases, as well as for other hepatoprotectors, usually does not provide full cure, and when the preparations are cancelled, there are often recurrences or exacerbation of liver diseases, including because of persistent disturbance of intestine biosteriosis, which is stubborn in a number of diseases of the gastrointestinal tract organs and liver.

In recent years, the concept of unity of all processes taking place in gastrointestinal tract pathology has been getting increased recognition in gastroenterology. Within the framework of this concept, one of the most important components of this normal state is normalization of colon microflora.

Microflora of the gastrointestinal tract (GIT) and the liver closely interact in processes of organism detoxification. Microbiota biofilm is the first one to get in contact and subsequent metabolic reactions with all substances entering the body with food, water or atmospheric air. Microbiota converts chemical substances to non-toxic end products or to intermediate compounds that are easily broken down in the liver and then eliminated from the body.

The body has two main detoxifying organs—the liver that performs body protection by means of oxidation reactions, and digestive tract microflora which uses for these purposes hydrolytic reduction processes. Disturbance of interaction of these systems results in mutual functional and structural changes in them and the body as a whole.

This is why enterohepatic circulation of various organic and inorganic substances can be, without exaggeration, considered among cardinal homeostatic mechanisms. Decrease of the detoxification function of GIT microflora dysbiosis, caused by various pathogens (drugs, food, stress, etc.) increases the load on enzyme systems of the liver, and under certain conditions facilitates the appearance of metabolic and structural changes in it.

In the case of disbalance of the digestive tract microecology, increased proportion of potentially pathogenic gram-negative bacteria results in substantial accumulation of endotoxins in the lumen of the intestine.

As endotoxins penetrate the local blood circulation system through intestine mucosa and then enter the liver through the portal vein, they damage hepatocites or potentiate adverse effects of other toxicants.

Ninety percent of all endotoxins are freed facultatively by gram-negative bacteria. Endotoxins damage cell membranes, disturb ion transport, cause fragmentation of nucleic acids, induce formation of products of free radical oxidation, initiate apoptosis, etc. (Gracheva, N. M., et al, Chilak-Forte in Complex Treatment of Patients With Acute intestinal infections and Chronic Diseases of Gastrointestinal Tract With Effects of Dysbacteriosi, Consilium medicum. 2004, No. 1, pp, 31-34).

Therefore, one of the possible ways to correct disturbances in the complex of microbiota and liver interaction is to fight intestine dysbiosis.

Then, known is the method for normalization of intestinal microflora by oral (per os) administration of probiotics—live bacteria, species and genera normally colonizing the colon of humans and other mammals (V. F. Dyomin et al.

The Experience of Using Biophitocorrection in Children With Disbiosis, see Journal of Modern Pediatrics, 2003, No. 3, vol. 2, pp, 33-36. However, the use of probiotics in the form of monotherapy does not produce sustainable effects because of the "foreignness" of bacteria strains, and their fairly rapid elimination (3-5 days) after stopping taking the medicinal agent (MP).

Other preparations used for correction of disturbances of intestinal microbiota—prebiotics do not have this shortcoming.

Probiotics, among other things, include a lot of oligosaccharides that are not utilized by human organism because the intestine does not have its own enzymes that break up such sugars. Among non-digestible oligosaccharides are, in particular, fructooligosaccharides (FOS), maltooligosaccharides, galactooligosaccharides, inulin, lactulose and some other oligosaccharides that can be used as preblotics (Sheveleva, S. A., Probiotics, Prebiotics and Probiotic Products. State of the Art.>≤[Journal of Nutrition], 1999, No, 2, pp. 33-39; Shoat K et al. Prebiotic galactooligosaccharides reduce adherence of Enteropathogenic *Escherichia coli* to tissue culture cells. Infect Immim., 2006, Sep, 18. Abstr.).

As far as their chemical structure is concerned, FOS are oligofructosaccharides, wherein β-, D-fructofuranose residues are connected to each other by β-2, 1-glycoside bonds, and on one end of the chain they have α-glucose residue connected to fructose by α-1, 2 bond.

They can he considered derivatives of saccharose, with from 1 to 3 fructofuranose residues connected to its fructose part by β-2, 1 bonds. The main components of FOS are 1-chestose (GF2), nistoze (GF3) and IF-fructofuranosylnistose (GF4).

FOS have a pronounced prebiotic effect—they are not digested in upper GIT, suppress growth of putrid microflora, facilitate normalization of blood pressure and the level of lipids in blood, improve adsorption of calcium and magnesium, increase immunity, have a beneficial effect on constipation and purulent processes, and prevent colon cancer.

Like all prebiotics, FOS are not hydralized by GIT ferments, are not absorbed in the small intestine and, entering the colon unchanged, are a selective substrate for growth of normal microflora.

Lactulose is a disaccharide consisting of galactose and fructose (4-0-D-galactopyranosyl-D-fructose). In vivo, lactulose in small quantities can form when milk is heated to temperatures above 100° C. Lactulose is very soluble in water and about 1.5-2 times sweeter than lactose.

The prebiotic effect of lactulose increases the volume of colon contents, decreases pH, decreases ammonia content in the colon and increases content of short-chain fatty acids, particularly propionic acid (ZDUNCZYK Z et al, Physiological effects of lactulose and inulin in the caecum of rats. Arch Anim Nutr., 2004, Vol. 58(1), $_{pp.}$ 89-98).

Also known is the lactulose effect on intestinal microflora—increasing the number of bifidobacteria with increased activity of microbial β-galatosidases (BOUCHNIC Y. et al. Prospective, randomized? Parallel-group trial to evaluate the effects of lactulose and polyethylene glycol-4000 on colonic flora in chronic idiopathic constipation. Aliment, Pharrnacol. Ther., 2004, Vol. 19(8), pp, 889-899).

Being a prebiotic, until now lactulose has at the same time been used in therapy mainly or even exclusively as a mild and effective laxative. The laxative effect of lactulose is due to its prebiotic effect and is caused by increased volume of colon contents (by about 30%) because of the increase in bacterial population.

For instance, known is the method for normalization of disorders of intestinal microflora that includes the use of prebiotics, particularly indigestible oligosaccaride (lactulose, FOS, etc.) (JP 2003-155242 of May 27, 2003).

In literature, there is very little information about attempts to use prebiotics for treatment of liver diseases.

According to published data (Nikitin, I.G. et al., Duphalac (Lactulose) in Treatment of Intestinal Dysbiosis in Nonalcoholic Steatohepatitis, see Clinical Prospects of Gastroenterology, Hepatology, and Coloproctology], 2002, No. 1, pp, 24-29; Savelev, V. S., Lipid Distress Syndrome in Surgery and Bulletin of the Russian Military Medical Academy, 1999, No. 1, pp. 35-39, their use as mono-preparations is by itself has little effect when attempting to treat liver diseases because in this case the damage to cells and, accordingly, to functions of damaged liver tissue is not completely eliminated.

The therapeutic effect of only using prebiotics occurs after a fairly long period, and in this case complete restoration of disturbed lipid metabolism and particularly of cholesterol metabolism is not achieved. Moreover, in the referenced studies lactulose was used in large doses (on the order of 30 ml of concentrated syrup per person) that are known not as much as prebiotic but rather laxative doses.

Usually, lactulose is used in hepatology in such large doses mainly to alleviate symptoms of liver encephaiopathy, i.e. in palliative symptomatic alleviation of condition in patients with already practically incurable conditions (advanced stage cirrhoses). In these situations, normalization of intestinal microflora cannot provide any long-term effect.

Therefore, in schemes of therapy of various diseases, the schemes of complex application of various groups of medicinal agents, for instance, immunomodulators and antibiotics, choleretics, etc. are ever more widely used.

In this respect, particularly known is the method for treatment of chronic non-calculus cholecystitis with manifestations of dysbiosis due to the use of combination of a hepatoprotector (glutargin) and an eublotic (bifiform) (UA 70018 of Sep. 15, 2004).

However, the therapeutic result of this combination is short-term due to the noted earlier limitations related to the use of probiotics. Also known is the method for treatment of liver diseases with cholestatic syndrome by using a combination of a phytogenic hepatoprotector (extract from *Silbum marianum*) with a probiotic strain of *Lactobacillus bulgarinii* and some other substances (BG 108250U of Apr. 30, 2005).

However, in this case too, the positive therapeutic effect is relatively short-term.

Known is the method for correction of Savelev's lipid distress syndrome using complex therapy including a phytogenic hepatorpotector—gepabene, and metabolite probiotic chilac-forte (Petukhov, V. A., Liver Function Abnormality And Dysbiosis in Lipid Distress Syndrome. PM Figure US20110312910A1-20111222-P00019 [RMZh], 2002, No. 10, Vol, 4, pp. 158-160).

However, in this analogue neither the scheme of treatment using these means nor their doses or ratios are specified, nor the interaction of the medicinal agents used is shown.

Also known is the use for treatment of liver diseases of a combined preparation comprising alkaline sphingomyelinase as the main acting agent, and various substances, including substances from the class of probiotics (*Lactobacillus acidophilus, Lactobacillus brevis, Lactobacillus buchneri, Lactobacillus casei, Lactobacillus catenaforme*) and UDCA, as additional means (EA 5166 of Dec. 30, 2004).

In the above analogue, the leading roles is played by sphingomyelinase (a lysosomal enzyme), which is used for prevention and/or treatment of various diseases from the following group: small intestine disorder, malignant tumors, immune system disturbance, inflammations and desquamation of the mucous membrane of the small intestine, conditions associated with disturbances in the synthesis of cholesterol, disturbances of absorption ability of the small intestine, and allergy diseases of the small intestine.

Herein, said pharmaceutical composition includes as additives probiotics (Lactobacillus acidophilus, Lactobacillus brevis, Lactobaciius casei, etc.), ursodeoxycholic acid—a bile acids derivative, and a prebiotic—lactulose.

But the patent description does not disclose the role of these additives in treatment of liver diseases, and there is no scientific justification of including them in this composition.

The use of the pharmaceutical composition for treatment of said diseases is not without the main shortcoming—a short-term effect, caused by an exogenous probiotic strain. Herein, prebiotic components present in the composition are to a large degree utilized by said introduced exogenous strain.

In addition, inclusion in the composition of a large number of components with different type of action not just does not make it possible to evaluate their role and therapeutic effect—it does not preclude mutual antagonism of such effects either, which increases the probability of individual variations in the reaction to administration of such large number of preparations.

The closest analogue of the claimed invention is the agent or component that improves the liver function, acts as the methyl group donor, includes a not easily assimilated oligosaccharide that comprises galactose, and is used as a functional nutrition product (JP 2003-155242 of May 27, 2003).

Herein, the methyl group donor is selected from the group of amino acids that includes S-adenosylmethionine, and the galactose-containing oligosaccharide is selected from the group that includes, among others, lactulose or galactooligosaccharide.

However, in the said patent the authors do not consider prebiotic effects of the composition at all, and in the proposed agent the authors reduced the role of the oligosaccharide component (and only supposedly at that) to elimination of ammonia-induced hepatoencephalopatic intoxication.

By that, the authors of the closest analogue do not link the lipid metabolism normalizing effect of compounds—the donors of methyl groups to normalization of the condition of intestinal microbiocenosis, and the examples provided do not mention this condition at all.

The lack of understanding of inseparable interrelation of the condition of intestinal microbiocenosis and lipid metabolism reactions, and the role of representatives of normal microflora in breaking the vicious circie of enteropathogenic recirculation of bile acids does not make it possible to correctly select not just the component content of the compositions depending on the degree of disturbance of these most important components of the metabolic process, but also to control to the necessary degree the adequacy and effectiveness of the therapy of liver diseases that is performed.

By reducing the role of the first component of the composition just to the function of the methyl group donor the authors unreasonably ignore other mechanisms of disturbance of lipid metabolism, particularly of cholesterol metabolism, that play the most important role in the development of many liver diseases.

The distinction of the claimed method from the closest analogue is as follows;

the liver diseases that are different from the closest analogue and for treatment of which a real pharmaceutical composition has been developed are clearly defined;

a pharmaceutical composition has been developed that comprises a hepatoprotector and a prebiotic selected strictly from a limited number of representatives of these groups of medicinal agents; the advisability of simultaneous introduction of a hepatoprotector and a prebiotic in one pharmaceutical composition because of their synergistic effect on each other is demonstrated;

the ratio of the hepatoprotector an the prebiotic in the claimed pharmaceutical composition has been developed.

The objective of the invention is to achieve substantial positive effects in the form of accelerating normalization of the health status and reduction of the intensity of the disease symptoms in the case of complex treatment of individual liver diseases.

Said objective is achieved by using in therapy of liver diseases a combined (complex) medicinal agent containing a mixture of a hepatoprotector and a prebiotic substance, particularly oligosaccharides that are not digestible in the intestine.

The technical result the invention aims to achieve is to restore liver functions as soon as possible and prevent disease recurrences by restoring cholesterol metabolism and intestinal biocenosis caused by synergistic interaction of the hepatoprotector and the prebiotic, which also causes prevention of the hepatoprotector side effects.

As the hepatorpotector, the invention uses bile acids/bile acid salts selected from the following group: GCA, GCDCA, TCA, TDCA, UDCA, CDCA, and essential phospholipids.

The presence of a hepatoprotector and a prebiotic in the claimed pharmaceutical composition ensures pronounced and sustainable therapeutic effect due to the synergistic effect of the hepatoprotector and the prebiotic.

Synergistic effect of a hepatoprotector, for instance, UDCA, and a prebiotic is due to the fact that UDCA normalizes intestinal digestion not just of fats, but also of solid food, due to increased synthesis of bile acids and UDCA itself in the liver, which facilitates normalization of intestinal microflora, while the the prebiotic by itself facilitates microflora normalization due to the stimulation of growth of resident strains, which causes manifestation of immunity-stimulating effects and other effects of normal flora. This results in improvement of digestion properties and consequently in improved detoxification of exogenous toxins by own microflora, which also reduces the metabolic load on the liver and facilitates normalization of metabolism of fatty acids and cholesterol, which in turn has a stabilizing effect on all body cells, including hepatocites. Thus, combining bile acids or bile acid salts in one pharmaceutical composition with oligosaccharides that are not digestible in the small intestine and chosen from the following group: lactulose or FOS, maltooligosaccharides, galactooligosaccharides, inulin—makes it possible to restore the function of hepatocites and the liver as a whole due to normalization of intestinal biocenosis, which in turn ensures long-term stabilization of the achieved therapeutic result.

It is well known that in liver diseases and cholelithiasis with mainly cholesterol stones, one observes higher content of toxic products in patient's blood that enter blood from the colon, especially of ammonia a nitro compound that forms in the process of bacterial decomposition of protein by proteolytic microfiora in the colon, which increases the toxic load on the liver.

Thus, restoration of microflora in the intestine indirectly facilitates the increase decrease [sic] of the toxic load on the liver and the increase of UDCA in the liver, which in turn facilitates restoration of bile composition, particularly the increase of bile acids due to decreased synthesis of cholesterol by the liver, and this in turns prevents recurrences of the disease, particularly of cholelithiasis with mainly cholesterol stones.

Taking the above into account, active components in the presented pharmaceutical composition mutually amplify the therapeutic properties each of them has.

The claimed pharmaceutical composition can include as the active agent various substances with hepatoprotective properties, particularly a hepatoprotector selected from the following groups: amino acids or their derivatives, active hepatoprotective substances from milk thistle plant extracts (silimarin, silibinin), or essential phospholipids, or bile acids/bile acid salts selected from the following group: CA, CDCA, DCA, UDCA, HDCA, TUDCA, TCA, and GCA in the unit dose from 50 mg to 500 mg, and a prebiotic selected from the group of oligosaccharides non-digestible in a human intestine, such as lactulose, or fructooligosaccharide (FOS), or maltooligosaccharides, or galactooligosaccharides, or inulin, taken each in the effective therapeutic prebiotic dose, galactooligosaccharides, maltooligosaccharides or xylooligosaccharides, with the hepatoprotector to prebiotic ratio from 1:2 to 1:250.

The claimed pharmaceutical composition can be made in the form of tablets (coated or uncoated), or granules, or globules, or powder, or capsules, or suspensions, or emulsions, or gels.

In doing so, the claimed pharmaceutical composition can additionally comprise additives that are generally accepted in the pharmaceutical industry, such as microcrystalline cellulose or lactose, or corn starch, or potato starch, or hydroxypropylmethylcellulose, or carboxymethylcellulose, or oxypropylmethylcellulose, or oxypropylcellulose, or their pharmaceutically acceptable salts, or ludipress, or calcium stearate, or magnesium stearate, or ploysorbate, or polyvinyl pyrrolidone, or polyethylene glycol, or talcum, or titanium dioxide, or silicon dioxide.

The claimed composition is prepared by mixing the components comprising it, both active (the hepatoprotector selected from the following group: essential phospholipids or bile acids/bile acid salts, and the prebiotic) and additives selected from the following group: microcrystalline cellulose, or lactose, or corn starch, or potato starch, or hydroxypropylmethylcellulose, or carboxymethyleellulose, or oxypropylmethylceliulose, or oxypropylcellulose, or their pharmaceutically acceptable salts, or ludipress, or calcium stearate, or magnesium stearate, or polysorbate, or polyvinyl pyrrolidone, or polyethylene glycol, or talcum, or titanium dioxide, or silicon dioxide.

The claimed pharmaceutical composition is administered orally, washed down with large amount of water, for a period from 1.5 to 3 months.

The claimed pharmaceutical composition can he used for treatment of patients with liver diseases selected from the following group: cholelithiasis with mainly cholesterol stones, alcoholic and non-alcoholic steatohepatitis, primary biliary cirrhosis, gall bladder cholesterosis, and drug-induced and toxic liver injury, and it makes it possible to achieve long-term remission of the disease in a relatively short time period (from 6 to 12 weeks).

Herein, the therapeutic effectiveness is from 89% to 95%.

The claimed pharmaceutical composition does not have contraindications and can be used for treatment of patients with liver diseases listed above, including against the background of severe concomitant diseases (except advanced stages of liver cirrhosis, malignant tumors of gastrointestinal tract or other organs), regardless of patient's age.

The claimed composition does not have significant side effects, because the active components in the pharmaceutical composition are used in small and medium unit therapeutic doses and during a fairly short time period.

The proposed versions of the composition are characterized by low cost and are therefore affordable for all categories of patients.

Patient treatment is performed outpatient and does not require the patients to keep bed rest or semi-strict bed rest regimen, which makes it possible for patients to lead normal life.

The proposed pharmaceutical composition can be successfully used not just for treatment but also for prevention of exacerbations of liver diseases selected from the following group: cholelithiasis with mainly cholesterol stones, alcoholic and non-alcoholic steatohepatitis, primary billiary cirrhosis, gall bladder cholesterosis and drug-induced and toxic liver injury, due to restoration of the structure and function of both hepatocites and function of the liver as a whole caused by normalization of intestinal microflora. The effect of the proposed pharmaceutical composition in a certain dose on the body stipulates gradual and increased enhancement of the therapeutic effect and connecting new levels of homeostasis regulation—the sub-cell, inter-cell, tissue, organ, system and body level, due to restoration of lipid metabolism, particularly cholesterol metabolism because of normalization of intestinal microbiocenosis.

During treatment, which is performed outpatient, it is recommended that the patient keep at least three meals a day regimen during the entire treatment period; it is not recommended to take alcohol, fatty and spicy food and other medicinal agents; fasting and hard physical work are prohibited.

The final diagnosis is determined based on additional types of examinations (USE of the liver or radiology of bile passages) and laboratory blood tests (biochemistry: cholesterol and its fractions, biliburin and its fractions, alkaline phosphotase, GPT, AST, ESR, etc.).

We examined 60 patients. In all patients, clinical symptoms of liver injury with various degree of manifestation had been found: ochrodermia of skin and sclera, skin itch, sense of discomfort or feeling of weight in the right hypochondrium, dyspeptic effects—nausea, anorexia, vomiting, weakness, atony, change of the color of urine (darker) and stool (loosening or diarrhea).

All patients had been treated earlier either outpatient or inpatient, using various medicinal agents. Most patients (37 out of 60) had concomitant diseases: chronic gastroduodenitis and cardiovascular system (CVS) diseases: hypertensive disease (HD), ischemic heart disease (IHD); lung diseases: pneumosclerosis, bronchial asthma (BrA), etc. Besides, in 85% of patients concomitant disturbances of the state of colon biocenosis were identified. For all patients in experimental groups (50), treatment using the claimed pharmaceutical composition was performed in the dosing regimen that had been developed: 3 times a day at meal time for 1.5-3.0 months.

By the end of the 2nd week, the detoxification and synthetic function of the liver had been restored in all 50 patients regardless of the character of liver injury, against the background of restoration of intestinal biocenosis.

All patients noted relief of discomfort in the right hypochondrium and improved general health as early as by the 5th day. By the start of the 2nd week the disappearance of dyspeptic disorders, restoration of appetite, normalization of urine and stool, disappearance of skin itch and restoration of the original skin color against the background of significant improvement in general condition and mood was observed subjectively in all patients; with this, the simultaneous relief or disappearance of concomitant pathology symptoms were noticed. In biochemical blood tests by the end of the 3rd week, normalization of all biochemical indexes, including those that characterize liver operation and lipid metabolism was noted.

EXAMPLES OF EMBODIMENT OF THE METHOD

1. Patient I., Male, 46 Years Old

On admission, complaints of aching pain in the right hypochondrium, radiating to the right shoulder, appearing 3-4 hours after consuming fatty food, or after a lavish meal, or after physical exertion; of general weakness, anorexia, nausea, periodic vomiting, feeling of bitterness in the mouth, stool loosening, sometimes diarrhea, skin itch, change of the color of urine (darker) and stool (lighter).

From the anamnesis: cholelithiasis for 10 years. Has not been operated. Has been treated outpatient, without much effect. Worsening after physical exertion.

Objectively: supernutrition, weight 75 kg, height 167 cm, skin pale, with traces of scratching on the back and abdomen, Icteric sclera.

Abdomen soft and painful at the Kehr point, Kehr's, Mussy's and Murphy's symptoms positive. Liver at the edge of the coastal arch. Vesicular breathing in the lungs. Breathing rate 18 a minute.

Cardiac border within the age norm. Sounds moderately deadened, rhythm regular, heart rate 78 a minute, BP 140/85 mm Hg.

Pasternatsky's syndrome negative on both sides. Provisional diagnosis: Chronic cholecystitis in the exacerbation phase.

Examination:

Complete blood count: Hb 123 g/l; erythrocytes (ER) 4.11×1012/l; color index (CI) 0.89; leukocytes 4.0×109/l; stab (S) leukocytes (L) 2%; segmental leukocytes (S) 46%; eosinophils (E) 5%; lymphocytes (L) 45%; monocytes (M) 2%; ESR 40 mm/h. Complete urinalysis: relative density 1016; no protein or glucose detected; leukocytes 0-1-3 in field of view; erythrocytes 0 in field of view; urine amilase 16.2 mgs/l.

Coprogram: muscle fibers without striation—a little; fatty acids—moderate amount; undigested phytogenic fiber—a lot; starch; isolated cells.

Feces on dysbacteriosis: Reduction of the number of bifidobacteria and lactobacilli, respectively: 105/g and 106/g, due to increase of *Candida* fungi. Blood biochemistry: bilirubin and its fractions: total bilirubin (TB)-22.8 µmol/l (N-3.4-20.5 µmol/l); conjugated bilirubin (CB)-3.8 µmol/l (N-0.85-3.4 µmol/l), non-conjugated bilirubin (NCB)-11.7 µmol/l (N-2.56-10.3 µmol/l); thymol test (TT)-12.1 units (N-4 units), ACT-79 units (N-60 units) GPT-72 nits/N-50 units), thymol test (TT)-1.7 units (N-4 units), alkaline phosphatase (ALP)-362 units (N-up to 295 units), CCC 15.3; sugar 3.5 mmol/l(N-4.4-6.6 mmol/l);

cholesterol and its fractions; total cholesterol (TC)-5.5 mmol/l (N-3.65-5.2 mmol/l), high-density lipids cholesterol (HDLC)-0.8 mmol/l (N-0.9-1.9 mmol/l), low-density lipids cholesterol (LDLC)-3.2 mmol/l(N-1.91-2.6 mmol/l), cholesterol atherogenic ratio (CAR) 3.5 c.u. (N-up to 3 c.u.), CCC 15.3 (N-up to 12);

protein fractions: total protein 67 g/l (N 65-85 g/l); albumins 34 g/l (N-36-50 g/l);

antinuclear antibodies; AMA titer 1:10;

coaguiogram: PTR 24 s-79%; thrombine clotting time 35 s; free heparin 12 s; fibrinogen 2.2 g/l; fibrinotytic activity>240 min.

Coprogram: dysbacteriosis due to reduction of lactobacilli and bifidobacteria: lactobacilli (105) (N>=107/g), bifidobacteria (107) (N>=109).

Radiography of the aver and bile passages—indirect signs of calculous cholecystitis, stones do not contrast, Recommended: USE of the liver and gallbladder.

USE of the liver—chronic cholesistisis, cholesterol stones: 0.9, 1.2, 1.5, 1.3 mm, edges even.

EKG—sinus rhythm, signs of moderate left ventricular hypertrophy, BP 150/85 mm Hg; heart rate 74 a minute.

Final diagnosis: Lipid metabolism disorder, hypercholesterinemia. Chronic calculous cholecystitis (cholesterol stones) in the exacerbation phase.

Treatment: the use of the claimed composition, wherein the active agents are a hepatoprotector—UDCA and lactulose in the ratio of 1:2 (unit dose of UDCA is 325 mg), orally 3 times a day at meal time for 1.5 months against the background of diet No. 5.

Follow-up examination in 1.5 months:

In USE: isolated stones, 1 and 2 mm in size.

According to laboratory examination, no pathology detected.

Recommended: continue the therapy for up to 3 months.

After 3 months: in USE—signs of chronic cholecystitis, no concrements.

Conclusion: chronic cholecystitis in the remission phase.

2. Patient B., Male, 45 Years Old

On admission, complaints of anorexia, weakness, nausea, periodic vomiting, aching pain in the right hypochondrium after a large or fatty meal. In anamnesis: chronic alcoholism. Primary biliary cirrhosis. Had been treated irregularly.

Objectively: subnutrition. Dry skin, hot to the touch. Light yellow skin, icteric sclera.

Above the lungs—pulmonary bandbox sound. Diminished breath sounds, diffused dry rales over the entire lung surface. Breathing rate 20 a minute.

Cardiac border expanded 1.0 cm to the left. Deadened sounds. Regular rhythm, second sound accent above the aorta.

Soft abdomen, the right edge of the liver protrudes 2.0 cm from under the coastal arch, the edge is solid. Spleen not enlarged.

Pasternatsky's syndrome doubtful.

Provisional diagnosis: primary biliary cirrhosis?

Examination:

Complete blood count: Hb 117 g/l; erythrocytes (Er) 3.5×10/l; color index (Cl) 0.9; leukocytes 4.0×10%; stab (S)-17%, leukocytes (L) 6%; segmental leukocytes (C) 36%; eosinophils (E) 5%; lymphocytes (L) 35%; monocytes (M) 1%; ESR 40 mm/h.

Complete urinalysis: relative density 1012; no protein or glucose detected; leukocytes 0-2-3 in field of view; erythrocytes 0-2 in field of view; urine amilase 14.7 mgs/l.

Coprogram: muscle fibers without striation—a little; fatty acids—moderate amount; phylogenic fiber.

Blood Biochemistry:

bilirubin and its fractions: total bilirubin (TB)-28.4 µmol/l (N-3.4-20.5 µmol/l); conjugated bilirubin (CB)-4.8 µmol/l (N-0.5-3.4 µmol/l), non-conjugated bilirubin (NCB)-15.0 µmol/l (N-2.56-10.3 µmol/l);

thymol test (TT16.1 units (N-4 units), ACT-90 units (N-60 units) GPT-74 units (N-50 units), alkaline phosphatase (ALP)-700 units (N-up to 295 units), sugar 6.6 mmol/l (N-44-6.6 mmol/l); cholesterol and its fractions: total cholesterol (TC)-5.9 mmol/l (N -3.65-5.2 mmol/l), high-density lipids cholesterol (HDLC)-10.8 mmol/l (N-0.9-1.9 mmol/l), low-density lipids cholesterol (LDLC)-3.6 mmol/l (N-1.91-2.6 mmol/l), cholesterol atherogenic ratio (CAR) 3.9 c.u. (N-up to 3 c.u.), CCC 16.3 (N-up to 12); (norm up to 50); protein fractions: total protein 63 g/l (N 65-85 g/l); albumins 34 g/l (N36-50 g/l;

antibodies: AMA in titer 1:45;

coaguiogram: PTR 24 s-79%; thrombine clotting time 31 s; free heparin 11 s; fibrinogen 2.0 g/l; fibrinolytic activity>221 min, Feces on dysbacteriosis: reduction of lactobacilli and bifidobacteria: lactobacilli (104), bifidobacteria (106).

Radiography of the liver and bile passages—the liver size increased by 2.5 cm due to the right lobe, distinct edges, indirect signs of biliar cirrhosis. Recommended: USE of the liver and gallbladder.

USE of the liver—signs of slight fatty infiltration of the liver and gallbladder cholesterosis. Pancreas not enlarged. Intra- and extrahepatic bile ducts not dilated. No signs of portal hypertension detected.

No portal hypertension detected [sic].

Liver biopsy: Dilated portal tracts infiltrated by lymphocytes, plasma cells, macrophages and eosinocytes. Among the cells of portal tract infiltrates there are formed lymphoid follicles. Infiltrates are detected in walls of some intralobular bile ducts. Here and there, the integrity of the bile ducts basic membrane is violated. Near damaged bile ducts there are granulomas built of epithelioid and gigantic multinucleate cells.

Conclusion: Biliary Cirrhosis.

EKG—sinus rhythm, signs of moderate left ventricular hypertrophy, BP 150/85 Hg; heart rate 76 a minute.

Final diagnosis: lipid metabolism disorder, hypercholesterinemia. Primary biliar cirrhosis.

Treatment: the use of the claimed composition, wherein the active agents are a hepatoprotector—CDCA, and FOS in the ratio of 1:250 (unit dose of CDCA is 250 mg), orally 3 times a day at meal time for 1.5 months against the background of diet No. 5.

Follow-up examination in 1,5 months:

In USE: positive dynamics—reduction of fatty infiltration of the liver. In blood tests: reduction of hypercholesterinemia OX-4.6 mmol/l, HDLC-1.2 mmol/l, CCC 13.2; TB-21.5 µmol/l, AMA 1:30; total protein-72 g/l, albumins-34%, blood sugar 5.3 mmol/l, alkaline phisohatase-301 units, ACT-70 units, GPT-62 units, TT-8.1 units.

Feces test on dysbacteriosis: lactobacilli 106 , bifidobacteria-107.

Recommended: continue the therapy for up to 3 months.

After 3 months—AMA 1:15, bifidobacteria 109/g, lactobacilli 107/g.

Conclusion: first degree primary biliary cirrhosis (significant positive dynamics).

3. Patient F., Female, 50 Years Old

On admission: complaints of apparent weakness, feeling of weight and aching pain in the upper right abdomen area that appear for no apparent reason, anorexia, nausea, periodic vomiting, feeling of bitterness in the mouth, stool softening, sometimes diarrhea, skin itch, changed color of urine (lighter) and stool (lighter).

From anamnesis: has had type 2 diabetes for 15 years, has been taking bukarban, a hypoglycemic agent. Has been under medical supervision by an endocrinologist and the district physician. Has been undergoing regular inpatient treatment at the endocrinology department, but without much effect. Associates the latest aggravation with virus infection (protracted course; complication: acute bronchitis, was taking antibacterial agents—cephalosporins).

Objectively: supernutrition—third degree obesity, body mass index (BMI) 34, pale skin, with traces of scratches on the abdomen and inner thighs. Icteric sclera, Abdomen greatly increased in size; soft, painful at Kehr's point. The liver protrudes 2.5 cm from under the coastal arch, the edge is solid. Spleen not enlarged.

Diminished vesicular breathing in the lungs (because of fatty tissue). Breathing rate 22 a minute.

Heart borders extended 1.0 cm to the right, 1.5 cm to left. Deadened sounds, regular rhythm, soft systolic murmur over the apex of the heart. Heart rate 76 a minute, BP 160/85 mm Hg.

Pasternatsky's symptom doubtful on both sides.

Provisional diagnosis: fatty hepatosis (?), type 2 diabetes, third degree obesity.

Examination:

Complete blood count: Hb 121 g/l; erythrocytes (Er)-4.15×1012/l; color index (CI)-0.89; leukocytes-3.8×10/l; stab (S) leukocytes (L)-7%; segmental leukocytes (S)-40%; eosinophils (E)-5%; lymphocytes (L) 45%; monocytes (M) 3%; ESR 39 mm/h. Blood glucose-6.8 mmol/l.

Complete urinalysis: relative density 1016; protein—traces; leukocytes 3-5 in field of view; erythrocytes 0 in field of view; urine amylase 16.2 mgc/l. Coprogram: muscle fibers without striation—a little; fatty acids—moderate amount; undigested phytogenic fiber—a lot; starch; isolated cells.

Feces on dysbacteriosis: Reduction of the number of bifidobacteria and lactobacilli, 105/g and 106/g (respectively) due to increased *Candida* fungi.

Blood Biochemistry:

bilirubin and its fractions: total bilirubin (TB)-27.0 µmol/l (N 3.4-20.5 µmol/l); conjugated bilirubin (CB)-3.6 µmol/l (N-0.85-3.4 µmol/l, non-conjugated bilirubin (NCB)-11.2 µmol/l (N-2.56-10.3 µmol/l);

thymol test (TT)-8.0 units (N-4 units), ACT-69 units (N-60 units) GPT-76 units (N-50 units), thymol test (TT)-1.7 units (N-4 units), alkaline phosphatase (ALP)-346 units (N-up to 295 units), CCC 15.3; sugar 6.9 mmol/l, (N-4.4-6.6 mmol/l);

cholesterol and its fractions; total cholesterol (TC)-5.9 (N-3.65-5.2 µmol), high-density lipids cholesterol (HDLC)-0.8 (N-0.9-1.9 mmol/l), low-density lipids cholesterol (LDLC)-3.6 mmol/l (N-1.91-2.6 mmol/l), cholesterol atherogenic ratio (CAR) 3.8 c.u. (N-up to 3 c.u.), CCC 16.3 (N-up to 12);

triglycerides: 1.94 mmol/l (N-0.45-1.82 mmol/l)

protein fractions: total protein 67 g/l (N-65-85 g/l); albumins 33 g/l (N-36-50 g/l).

coagulogram: PTR 24 s-79%; thrombine clotting time 35 s; free heparin 12 s; fibrinogen 2.2 g/l; fibrinolytic activity>240 min.

Coprogram: dysbacteriosis due to reduction of lactobacilli and bifidobacteria—lactobacilli (104) (N>=107/g), bifidobacteria (106) (N>=109/g).

Radiography of the Liver and Bile Passages:
uniform enlargement of the liver, no concrements.

Recommended: USE of the liver and bile passages.

USE of the liver—second degree hepatomegalia. Pancreas not enlarged.

Intra- and extrahepatic bile ducts not dilated. Signs of portal hypertension.

Esophagogastroduodenoscopy: esophageal veins dilatation B/3.

EKG—sinus rhythm, signs of moderate left ventricular hypertrophy, incomplete right bundle-branch block, BP 160/85 mm Hg;

Heart rate 74 a minute.

Final diagnosis: lipid metabolism disorder, triglyceridernia. Fatty hepatosis. Type 2 diabetes. third degree obesity.

Treatment: the use of the claimed composition, wherein the active agents are a hepatoprotector—essential phospholipids, and FOS in the ratio of 1:50 (the unit dose of essential phospholipids is 50 mg), orally 3 times a day at meal time for 1.5 months against the background of diet No. 5.

Follow-up examination in 1.5 months:

The patient notes reduction of skin itch, increased activity; itch practically does not bother her, notes a 5 kg weight reduction. In USE: reduction of the liver size noted. Conclusion: fatty hepatosis, first degree hepatomegaly.

According to laboratory examination, reduction of triglycerides-1.82 mmol/l and total cholesterol-5.0 mmol/l, blood sugar has normalized-4.9 mmol/l, In feces analyses, significant increase of lactobacilli and bifidobacteria-107/g and 109/g (respectively), is noted; no *Candida* fungi detected.

Recommended: continue the therapy for up to 3 months.

After a 3 months, in USE—signs of moderate hepatomegaly. Blood tests—no peculiarities. Intestinal microflora has been restored: lactobacilli 107/g, bifidobacteria 109/g.

Conclusion: fatty hepatosis, signs of moderate hepatomegaly. Type 2 diabetes; compensation; third degree obesity.

Example 4

Testing Acute Toxicity of the Compositions

The composition of UDCA and lactulose in the ratio of 1:2 (group 1), UDCA and FOS in the ratio of 1:50 (group 2), essential phospholipids (lecithin) and galactooligosaccharides in the ratio of 1:30 (group 3), ademethioninea and lactulose in the ratio of 1:50 (group 4) was administered orally to outbred white mice with body mass of 15-20 g.

The control group (group 6) was administered the equal amount of starch suspension. The animals were monitored for 4 days, and their general condition (appearance, mobility (activity), the regularity of food and water intake, the appearance and character of excrements) was recorded.

| Mixture (Group) | Maximum Amount of Administered Preparation (g) | Survival Rate (Alive/Died) | Appearance | Diet | Motility | Excrement Appearance And Character |
|---|---|---|---|---|---|---|
| 1 | 2 | 6/0 | N | N | N | N |
| 2 | 2 | 6/0 | N | N | N | N |
| 3 | 2 | 6/0 | N | N | N | N |
| 4 | 2 | 6/0 | N | N | N | N |
| 5 | 2 | 6/0 | N | N | N | N |
| 6 | 2 | 6/0 | N | N | N | N |

Based on the results of examination, no evidence of acute toxicity of each composition under the experimental conditions—all mixtures pertain to the class of low toxicity substances (LD50 values exceed 100 g/kg of body mass).

Thus, the claimed pharmaceutical composition that includes as active agents a hepatoprotector and a prebiotic selected from non-digestible in the intestine oligosaccharides can be recommended for use under clinical conditions for treatment and prevention of liver diseases selected from the following group: cholelithiasis, fatty hepatosis and non-alcoholic steatohepatitis, primary biliary cirrhosis, gall bladder cholesterosis, and drug-induced and toxic liver injury.

Example 5

This example shows the beneficiary properties of treatment of liver diseases (e.g., selected from cholelithiasis, fatty hepatosis and nonalcoholic steatohepatitis, primary biliary cirrhosis, gall bladder cholesterosis, and drug-induced and toxic liver injury), by administering compositions comprising a combination of UDCA and lactitol.

The compositions of (1) UDCA and lactitol in the ratio of 1:3 (Group 1), (2) UDCA and lactulose in the ratio of 1:3 (Group 2), and (3) UDCA alone (Group 3), were administered orally for Sprague-Dawley rats with a body mass of 220-240 g during 90 days on the background of a high-fat diet induced non-alcoholic hepatitis.

The control group (Group 4, n=14 in each group) was administered an equal amount of 1% methyl cellulose suspension.

The animals were monitored for 120 days on the background of continuous pathology induction. Administration of drugs began after 30 days from the beginning of diet supplementation (10 % lard and 2% cholesterol for each 100 g feed). The effect of therapy was assessed by biochemical parameters (ALT, AST, triglycerides) and liver histology.

On day 121, animals were euthanized and liver histology was performed. In the control group, 91.6% of animals developed steatosis. In Group 1 and Group 2, signs of steatosis, ballooning, and inflammation improved in 91.6% and 83.3% of rats, respectively; whereas, in Group 3, the percentage of improvement was only 50%.

On day 121, in Groups 1 and 2, levels of aspartate transaminase, alanine transaminase, and triglycerides were significantly lower than that of Groups 3 and 4.

Conclusion: the pharmaceutical composition of UDCA and lactitol improved steatosis in rat models of non-alcoholic steatohepatitis.

What is claimed is:

1. A method for treating and preventing recurrences of liver diseases in humans caused by a disturbance of lipid-cholesterol metabolism, wherein the liver diseases are selected from a group consisting of cholelithiasis with mainly cholesterol stones, alcoholic and nonalcoholic steatohepatitis, primary biliar cirrhosis, gall bladder cholesterosis, and drug-induced and toxic liver injury, the method comprising:

administering a composition orally on a patient, wherein the composition comprises a mixture of a hepatoprotector and a prebiotic combined together in effective doses in a ratio of 1:2 to 1:250 by mass of pure substances, wherein the hepaprotector comprises ursodeoxycholic acid (UDCA) and the prebiotic comprises lactitol, and delivering the UDCA and lactitol to the patient's liver.

2. The method of claim 1, wherein the administering occurs for 1 month.

3. The method of claim 1, wherein the administering occurs for 3 months.

4. The method of claim 1, wherein the administering occurs 3 times daily.

5. The method of claim 1, wherein the UDCA: lactitol ratio is between 1:2 and 1:250.

* * * * *